(12) United States Patent
Yu et al.

(10) Patent No.: US 11,813,237 B2
(45) Date of Patent: Nov. 14, 2023

(54) CREATINE, ITS DERIVATIVES, COMPOSITIONS AND METHODS OF USE THEREOF

(71) Applicants: Ruey J. Yu, Chalfont, PA (US); Eugene J. Van Scott, Abington, PA (US)

(72) Inventors: Ruey J. Yu, Chalfont, PA (US); Eugene J. Van Scott, Abington, PA (US)

(*) Notice: Subject to any disclaimer, the term of this patent is extended or adjusted under 35 U.S.C. 154(b) by 0 days.

(21) Appl. No.: 18/187,385

(22) Filed: Mar. 21, 2023

(65) Prior Publication Data

US 2023/0218555 A1    Jul. 13, 2023

Related U.S. Application Data

(60) Continuation of application No. 17/821,869, filed on Aug. 24, 2022, now Pat. No. 11,642,328, which is a division of application No. 17/655,813, filed on Mar. 22, 2022, now abandoned.

(60) Provisional application No. 63/169,584, filed on Apr. 1, 2021, provisional application No. 63/241,130, filed on Sep. 7, 2021.

(51) Int. Cl.
| | | |
|---|---|---|
| *A61K 31/198* | (2006.01) | |
| *A61K 45/06* | (2006.01) | |
| *A61P 17/00* | (2006.01) | |
| *A61P 17/04* | (2006.01) | |
| *A61P 17/06* | (2006.01) | |
| *A61P 29/00* | (2006.01) | |
| *A61P 25/06* | (2006.01) | |

(52) U.S. Cl.
CPC ............ *A61K 31/198* (2013.01); *A61K 45/06* (2013.01); *A61P 17/00* (2018.01); *A61P 17/04* (2018.01); *A61P 17/06* (2018.01); *A61P 25/06* (2018.01); *A61P 29/00* (2018.01)

(58) Field of Classification Search
CPC ...... A61K 31/198; A61K 31/22; A61K 45/06; A61K 47/26; A61K 9/0019; A61K 9/08; A61P 17/00; A61P 17/04; A61P 17/06; A61P 25/06; A61P 29/00
See application file for complete search history.

(56) References Cited

U.S. PATENT DOCUMENTS

| | | |
|---|---|---|
| 6,159,485 A | 12/2000 | Yu et al. |
| 2006/0269535 A1 | 11/2006 | Naidu et al. |

FOREIGN PATENT DOCUMENTS

| | | | | |
|---|---|---|---|---|
| WO | WO-2014019855 A1 | * | 2/2014 | ........... A23L 33/175 |

OTHER PUBLICATIONS

Allergy Insider, "What is eczema?", published online Aug. 10, 2018, https://www.thermofisher.com/allergy/us/en/living-with-allergies/symptom-management/eczema.html (Year: 2018).

* cited by examiner

*Primary Examiner* — Sarah Pihonak
(74) *Attorney, Agent, or Firm* — Ice Miller LLP

(57) ABSTRACT

The application describes creatine or its derivatives, compositions comprising the same, and uses thereof for topical or systemic administration to treat pain, itch, or eczema, or inflammation associated with a cosmetic or medical condition, disorder or disease in a human subject, wherein the inflammation causes the pain, itch, or eczema. In addition, the application describes clinical use of these compounds and compositions which can reduce or eliminate erythema, edema and tissue distortions associated with inflammation.

11 Claims, No Drawings

CREATINE, ITS DERIVATIVES, COMPOSITIONS AND METHODS OF USE THEREOF

CROSS-REFERENCE TO RELATED APPLICATIONS

This application is a continuation of Ser. No. 17/821,869 filed Aug. 24, 2022, which is a divisional of U.S. patent application Ser. No. 17/655,813 filed Mar. 22, 2022, which claims priority under 35 U.S.C. § 119 to U.S. Provisional Patent Application No. 63/169,584, filed on Apr. 1, 2021, and U.S. Provisional Patent Application No. 63/241,130, filed on Sep. 7, 2021, the disclosures of which are herein incorporated by reference in their entireties.

FIELD OF THE INVENTION

The application describes creatine or its derivatives, compositions comprising the same, and uses thereof for topical or systemic administration to treat pain, itch, or eczema, or inflammation associated with a cosmetic or medical condition, disorder or disease in a human subject. In addition, the application describes clinical use of these compounds and compositions which can reduce or eliminate erythema, edema and tissue distortions associated with inflammation.

BACKGROUND OF THE INVENTION

Creatine is thought to improve strength, increase lean muscle mass, and help the muscles recover more quickly during exercise. This muscular boost may help athletes achieve bursts of speed and energy, especially during short bouts of high-intensity activities such as weight lifting or sprinting. Creatine is N-methyl-N-guanylglycine, and has the following chemical formula (1):

$$H_2NC(=NH)N(CH_3)CH_2COOH \quad \text{Formula (1)}$$

Creatine has a molecular weight of 131. One gram of creatine monohydrate dissolves in 75 ml water, about 1.3%, and partially insoluble in alcohol or ether.

US2002/0161049 A1, published on Oct. 31, 2002 by Rima Kaddurah-Daouk et al. and entitled "Use of creatine or creatine analogs for the treatment of diseases of the nervous system," US2004/0102419 A1, published on May 27, 2004 by Rima Kaddurah-Daouk et al. and entitled "Use of creatine or creatine analogs for the treatment of diseases of the nervous system," and US2010/0303840 A1, published Dec. 2, 2010 by Rima Kaddurah-Daouk et al. and entitled "Use of creatine or creatine analogs for the treatment of diseases of the nervous system," describe the use of creatine, creatine phosphate or analogs of creatine, such as cyclocreatine, for treating diseases of the nervous system including diabetes, toxic neuropathies, Alzheimer's disease, Parkinson's disease, Huntington's, amyotropic lateral sclerosis and multiple sclerosis.

US2005/0227996 A1, published Oct. 13, 2005 by Rima Kaddurah-Daouk et al. and entitled "Use of creatine or creatine compounds for skin preservation," describes creatine compounds as energy generating systems, antioxidants for preservation of skin against adverse aging effects.

However, none of the prior art described the use of creatine derivatives of the current invention and compositions thereof to alleviate or eliminate pain, itch, eczema, or inflammation.

BRIEF SUMMARY OF THE INVENTION

The inventors have discovered that creatine or its derivative, with or without other pharmacological agents, is cosmetically or therapeutically effective for treating pain, itch, eczema, or discomfort associated with an inflammatory cosmetic or medical condition, disorder, or disease when administered topically or systemically to a human subject. More specifically, the inventors discovered that creatine or its derivative is therapeutically effective as an analgesic substance for eradicating pain, itch, or eczema associated with inflammatory neuropathic pain, itch, eczema, arthritis, migraine headache, acute common headache, osteoarthritis, psoriatic arthritis, rheumatoid arthritis, and various other pain, itch, or eczemas associated with inflammation in human subjects, when topically or systemically administered. The inventors have discovered and repeatedly confirmed that creatine or its derivative is therapeutically effective for topical or systemic administration to alleviate or eradicate pain, itch, or eczema associated with an inflammatory medical condition, disorder or disease in a human subject. The systemic administration includes parenteral injections, oral or nasal spray, and under the tongue administration (i.e., sublingual), to bypass liver digestion with oral administration.

In one general aspect, the present application relates to creatine or a derivative thereof of Formula (2):

$$H_2NC(=NR_1)N(CH_3)CH_2COR_2 \quad \text{Formula (2)}$$

or a pharmaceutically acceptable salt thereof or a solvate thereof,
wherein, $R_1$ is H or an acyl radical having up to 29 carbon atoms; $R_2$ is H, $OR_3$, $NHR_4$, or any other amino group containing radical having up to 10 carbon atoms; $R_3$ is H, an alkyl, aralkyl or aryl radical, wherein the alkyl, aralkyl or aryl radical has up to 19 carbon atoms; and $R_4$ is H, OH, an alkyl, aralkyl, aryl or acyl radical, wherein the alkyl, arakyl, aryl or acyl radical has up to 19 carbon atoms.

In some embodiments, $R_2$ is H, $OR_3$, or $NHR_4$, preferably H, OH, OEt, $OC_3H_7$, NHOH, or $NH_2$.

In some embodiments, $R_2$ is $NHNHR_5$; and $R_5$ is H, OH, an alkyl, aralkyl, aryl or acyl radical, wherein the alkyl, arakyl, aryl, or acyl radical has up to 19 carbon atoms.

In some embodiments, $R_2$ is $NHNH_2$, NHNHAc, $NHCONH_2$, $NH(C=NH)NH_2$, $NH(C=NH)NHNH_2$, $NHNH(C=NH)NH_2$, $NH(C=NH)NHNHAc$, NHNH(C=NH)NHAc, or $(H_3C)_2N(C=N)N(CH_3)_2$.

In another general aspect, the present application relates to a composition comprising creatine or a derivative thereof of Formula (2):

$$H_2NC(=NR_1)N(CH_3)CH_2COR_2 \quad \text{Formula (2)}$$

or a pharmaceutically acceptable salt thereof or a solvate thereof, and optionally a pharmaceutically or cosmetically acceptable carrier,
wherein, $R_1$ is H or an acyl radical having up to 29 carbon atoms; $R_2$ is H, $OR_3$, $NHR_4$, or any other amino group containing radical having up to 10 carbon atoms; $R_3$ is H, an alkyl, aralkyl or aryl radical, wherein the alkyl, aralkyl or aryl radical has up to 19 carbon atoms; and $R_4$ is H, OH, an alkyl, aralkyl, aryl or acyl radical, wherein the alkyl, arakyl, aryl or acyl radical has up to 19 carbon atoms.

In some embodiments, the composition is for topical administration.

In some embodiments, the composition is for systemic administration, including subcutaneous injection.

In some embodiments, the composition is used to alleviate pain, itch, or eczema, or inflammation in a human subject in need thereof.

In particular embodiments, the pain, itch, or eczema is associated with a medical condition, disorder or disease including arthritis (e.g., osteoarthritis, psoriatic arthritis, etc.), headache (e.g., migraine headache, hangover headache, etc.), dental pain, itch, eczema, lipoma, muscle pain, itch, eczema, pharyngitis, sprain, trauma, sunburn, and thermal burns.

In yet another general aspect, the present application relates to a method for treating pain, itch, or eczema, or inflammation in a human subject in need thereof, the method comprising administering to the human subject a composition comprising creatine or a derivative thereof of Formula (2):

  Formula (2)

or a pharmaceutically acceptable salt thereof or a solvate thereof, and optionally a pharmaceutically or cosmetically acceptable carrier, wherein, $R_1$ is H or an acyl radical having up to 29 carbon atoms; $R_2$ is H, $OR_3$, $NHR_4$, or any other amino group containing radical having up to 10 carbon atoms; $R_3$ is H, an alkyl, aralkyl or aryl radical, wherein the alkyl, aralkyl or aryl radical has up to 19 carbon atoms; and $R_4$ is H, OH, an alkyl, aralkyl, aryl or acyl radical, wherein the alkyl, arakyl, aryl or acyl radical has up to 19 carbon atoms.

In some embodiments, the composition is administered topically.

In some embodiments, the composition is administered systemically, including by subcutaneous injection.

In some embodiment, the method is for treating pain in the human subject.

In particular embodiments, the pain is associated with a medical condition, disorder or disease including arthritis (e.g., osteoarthritis, psoriatic arthritis, etc.), headache (e.g., migraine headache, hangover headache, etc.), dental pain, itch, eczema, lipoma, muscle pain, pharyngitis, sprain, trauma, sunburn, and thermal burns.

Other aspects, features and advantages of the invention will be apparent from the following disclosure, including the detailed description of the invention and its preferred embodiments, and the appended claims.

DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood by one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the term "treatment" or "treating" refers to amelioration, improvement, prophylaxis, or reversal of a disease or disorder, or at least one discernible symptom thereof. In certain embodiment, "treatment" or "treating" refers to amelioration, improvement, prophylaxis, or reversal of at least one measurable physical parameter related to the disease or disorder being treated, not necessarily discernible in or by the mamma! or subject. In another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder, In some embodiments, compounds and composition as described in the present application are administered as a preventative measure. As used herein, "prevention" or "preventing" refers to a reduction of the risk of acquiring a given disease or disorder.

Common or certain knowledge, scientific and medical terminologies can be readily found via internet, textbooks of chemistry, biochemistry, medicinal chemistry, pharmacology, dermatology and general medicine. The following are some examples. Robert K. Murray et al. eds. "Harper's Illustrated Biochemistry" 26th ed. Vol. I-II, McGraw Hill, 2003. Laurence L. Brunton et al. eds. "Goodman & Gilman's The Pharmacological Basis of Therapeutics" 12th ed. McGraw Hill Medical, 2011. Anthony S. Fauci et al. eds. "Harrison's Principles of Internal Medicine" $17^{th}$ ed., McGraw Hill Medical, New York, 2008. Abba J. Kastin, Ed "Handbook of Biologically Active Peptides" $2^{nd}$ ed. Academic Press, 2013. John Howl and Sarah Jones Ed "Bioactive peptides", CRC Press 2009.

Certain abbreviations and terms used herein include: Ac (acetyl), Ba (butanoyl), Bo (benzyloxycarbonyl), Bz (benzoyl), Fo (formyl), Hd (hexadecanoyl), He (hexanoyl), Hp (heptanoyl), Le (linoleic), Ln (linolenic), Na (nonanoyl), Oa (octanoyl), Pa (propanoyl), Pc (phenylacetyl), Pe (pentanoyl), Pg (pyroglutamyl); ethyl ester, OEt; propyl ester, OPr; and methyl ester, OMe; —NH(C=NH)NHNH$_2$, aminoguanidine radical; —NHNH(C=NH)NH$_2$, aminoguanidine radical with different attachment.

In one general aspect, the present application relates to creatine or a derivative thereof of Formula (2):

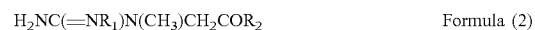  Formula (2)

or a pharmaceutically acceptable salt thereof or a solvate thereof, wherein, $R_1$ is H or an acyl radical having up to 29 carbon atoms; $R_2$ is H, $OR_3$, $NHR_4$, or any other amino group containing radical having up to 10 carbon atoms; $R_3$ is H, an alkyl, aralkyl or aryl radical, wherein the alkyl, aralkyl or aryl radical has up to 19 carbon atoms; and $R_4$ is H, OH, an alkyl, aralkyl, aryl or acyl radical, wherein the alkyl, arakyl, aryl or acyl radical has up to 19 carbon atoms.

A typical acyl radical and abbreviation suitable for use in the invention includes, but is not limited to, Ac (acetyl), Ba (butanoyl), Bo (benzyloxycarbonyl), Bz (benzoyl), Fo (formyl), Hd (hexadecanoyl), He (hexanoyl), Hp (heptanoyl), Le (linoleic), Ln (linolenic), Na (nonanoyl), Oa (octanoyl), Pa (propanoyl), Pc (phenylacetyl), Pe (pentanoyl), and Pg (pyroglutamyl).

In some embodiments, $R_1$ is H, Ac (acetyl), Ba (butanoyl), Bo (benzyloxycarbonyl), Bz (benzoyl), Fo (formyl), Hd (hexadecanoyl), He (hexanoyl), Hp (heptanoyl), Le (linoleic), Ln (linolenic), Na (nonanoyl), Oa (octanoyl), Pa (propanoyl), Pc (phenylacetyl), Pe (pentanoyl), or Pg (pyroglutamyl).

In some embodiments, $R_1$ is H, Ac (acetyl), Bz (benzoyl), or Pc (phenylacetyl).

In some embodiments, $R_2$ is H, $OR_3$, or $NHR_4$, preferably H, OH, OEt, $OC_3H_7$, NHOH, or $NH_2$.

In some embodiments, $R_2$ is $NHNHR_5$; and $R_5$ is H, OH, an alkyl, aralkyl, aryl or acyl radical, wherein the alkyl, arakyl, aryl, or acyl radical has up to 19 carbon atoms.

In some embodiments, $R_2$ is $NHNH_2$, NHNHAc, $NHCONH_2$, $NH(C=NH)NH_2$, $NH(C=NH)NHNH_2$, $NHNH(C=NH)NH_2$, $NH(C=NH)NHNHAc$, NHNH$(C=NH)NHAc$, or $(H_3C)_2N(C=N)N(CH_3)_2$.

In certain embodiments, $R_2$ is $NH(C=NH)NH_2$, $NH(C=NH)NHNH_2$, or $NHNH(C=NH)NH_2$.

Representative creatine or the derivatives in Formula (2) are listed in Table 1:

salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the application can form pharmaceutically acceptable salts with various amino acids. Suitable base salts include, but are not limited to, aluminum, calcium, lithium, magnesium, potassium, sodium, zinc, bismuth, and diethanolamine salts. For a review on pharmaceutically acceptable salts see Berge et al., 66 J. Pharm. Sci. 1-19 (1977), incorporated herein by reference.

Compounds of the present application can exist in solvated and unsolvated forms. The term "solvate," as used herein, means a physical association, e.g., by hydrogen bonding, of a compound of the application with one or more solvent molecules. The solvent molecules in the solvate can be present in a regular arrangement and/or a non-ordered arrangement. The solvate can comprise either a stoichiometric or nonstoichiometric amount of the solvent molecules. "Solvate" encompasses both solution-phase and isolable solvates. Compounds of the application can form solvates with water (i.e., hydrates) or common organic solvents. Exemplary solvates include, but are not limited to, hydrates,

TABLE 1

Representative Compounds

| Compound No. | Compound Name | Structure |
|---|---|---|
| C10 | creatine | $H_2NC(=NH)N(CH_3)CH_2COOH$ |
| C11 | creatinamide | $H_2NC(=NH)N(CH_3)CH_2CONH_2$ |
| C12 | ethyl creatinate | $H_2NC(=NH)N(CH_3)CH_2COOC_2H_5$ |
| C13 | N-acetyl creatine | $H_2NC(=NAc)N(CH_3)CH_2COOH$ |
| C14 | N-acetyl creatinamide | $H_2NC(=NAc)N(CH_3)CH_2CONH_2$ |
| C15 | N-acetyl ethyl creatinate | $H_2NC(=NAc)N(CH_3)CH_2COOC_2H_5$ |
| C16 | creatine aldehyde | $H_2NC(=NH)N(CH_3)CH_2CHO$ |
| C17 | N-acetylcreatine aldehyde | $H_2NC(=NAc)N(CH_3)CH_2CHO$ |
| C18 | N-benzoyl creatine | $H_2NC(=NBz)N(CH_3)CH_2COOH$ |
| C19 | N-benzoyl creatinamide | $H_2NC(=NBz)N(CH_3)CH_2CONH_2$ |
| C20 | N-benzoyl ethyl creatinate | $H_2NC(=NBz)N(CH_3)CH_2COOC_2H_5$ |
| C21 | N-benzoyl creatine aldehyde | $H_2NC(=NBz)N(CH_3)CH_2CHO$ |
| C22 | creatinoylguanidine | $H_2NC(=NH)N(CH_3)CH_2CONH(C=NH)NH_2$ |
| C23 | N-acetylcreatinoylguanidine | $H_2NC(=NAc)N(CH_3)CH_2CONH(C=NH)NH_2$ |
| C24 | creatinylaminoguanidine | $H_2NC(=NH)N(CH_3)CH_2CONHNH(C=NH)NH_2$ |
| C25 | N-acetylcreatinylaminoguanidine | $H_2NC(=NAc)N(CH_3)CH_2CONHNH(C=NH)NH_2$ |
| C26 | N-2-acetoxybenzoyl ethyl creatinate | $H_2NC(=NAb)N(CH_3)CH_2COOC_2H_5$ |
| C27 | N-2-acetoxybenzoyl creatine | $H_2NC(=NAb)N(CH_3)CH_2COOH$ |
| C28 | N-2-acetoxybenzoyl creatinamide | $H_2NC(=NAb)N(CH_3)CH_2CONH_2$ |
| C29 | N-acetyl propyl creatinate | $H_2NC(=NAc)N(CH_3)CH_2COOC_3H_7$ |
| C30 | N-2-acetoxybenzoyl propyl creatinate | $H_2NC(=NAb)N(CH_3)CH_2COOC_3H_7$ |
| C31 | N-phenyl acetyl creatine | $H_2NC(=NPc)N(CH_3)CH_2COOH$ |

Note:
Ac: acetyl; Ab: acetoxybenzoyl; Bz: benzoyl; Pc: Phenylacetyl; Guanidine: —NH(C=NH)NH$_2$; Aminoguanidine: —NHNH(C=NH)NH$_2$ or —NH(C=NH)NHNH$_2$.

The phrase "pharmaceutically acceptable salt", as used herein, means those salts of a compound of interest that are safe and effective for use in mammals and that possess the desired biological activity. Pharmaceutically acceptable ethanolates, methanolates, and isopropanolates. Methods of solvation are generally known in the art.

Compounds of the present application can be made or synthesized by any method known to those skilled in the art in view of the present disclosure. Methods of making creatine derivatives, such as by chemical synthesis, are well known to those of ordinary skill in the art in view of the present disclosure.

In another general aspect, the present application relates to a composition comprising creatine or a derivative thereof of Formula (2):

$$H_2NC(=NR_1)N(CH_3)CH_2COR_2 \qquad \text{Formula (2)}$$

or a pharmaceutically acceptable salt thereof or a solvate thereof, and optionally a pharmaceutically or cosmetically acceptable carrier,
wherein, $R_1$ is H or an acyl radical having up to 29 carbon atoms; $R_2$ is H, $OR_3$, $NHR_4$, or any other amino group containing radical having up to 10 carbon atoms; $R_3$ is H, an alkyl, aralkyl or aryl radical, wherein the alkyl, aralkyl or aryl radical has up to 19 carbon atoms; and $R_4$ is H, OH, an alkyl, aralkyl, aryl or acyl radical, wherein the alkyl, arakyl, aryl or acyl radical has up to 19 carbon atoms. A composition according to the invention can comprise creatine or any derivative thereof of Formula (2) or any pharmaceutically acceptable salt thereof or any solvate thereof described herein.

In some embodiments, $R_1$ is H, Ac (acetyl), Ba (butanoyl), Bo (benzyloxycarbonyl), Bz (benzoyl), Fo (formyl), Hd (hexadecanoyl), He (hexanoyl), Hp (heptanoyl), Le (linoleic), Ln (linolenic), Na (nonanoyl), Oa (octanoyl), Pa (propanoyl), Pc (phenylacetyl), Pe (pentanoyl), or Pg (pyroglutamyl).

In some embodiments, $R_1$ is H, Ac (acetyl), Bz (benzoyl), or Pc (phenylacetyl).

In some embodiments, $R_2$ is H, $OR_3$, or $NHR_4$, preferably H, OH, OEt, $OC_3H_7$, NHOH, or $NH_2$.

In some embodiments, $R_2$ is $NHNHR_5$; and $R_5$ is H, OH, an alkyl, aralkyl, aryl or acyl radical, wherein the alkyl, arakyl, aryl, or acyl radical has up to 19 carbon atoms.

In some embodiments, $R_2$ is $NHNH_2$, $NHNHAc$, $NHCONH_2$, $NH(C=NH)NH_2$, $NH(C=NH)NHNH_2$, $NHNH(C=NH)NH_2$, $NH(C=NH)NHNHAc$, $NHNH(C=NH)NHAc$, or $(H_3C)_2N(C=N)N(CH_3)_2$.

In certain embodiments, $R_2$ is $NH(C=NH)NH_2$, $NH(C=NH)NHNH_2$, or $NHNH(C=NH)NH_2$.

Representative creatine or the derivatives in Formula (2) are listed in Table 1 described above.

In a particular embodiment, the composition comprises N-acetyl ethyl creatinate.

In another particular embodiment, the composition comprises creatine monohydrate.

In another particular embodiment, the composition comprises HCl salt of ethyl creatinate.

According to embodiments of the present application, the composition comprises a therapeutically effective amount of creatine or a derivative thereof of Formula (2) or a pharmaceutically acceptable salt thereof or a solvate thereof. In view of the present disclosure, standard procedures can be performed to evaluate the effect of administration of a composition to a subject (e.g., determine whether a clinically observable beneficial effect is achieved), thus allowing a skilled artisan to determine the therapeutically effective amount of creatine or the derivative thereof of the pharmaceutically acceptable salt thereof or the solvate thereof. A clinically observable beneficial effect can be a situation that, when a composition of the invention is administered to a subject after symptoms to be treated are observable, the symptoms are prevented from further development or aggravation, or develop to a lesser degree than without administration of the composition of the invention. The clinically observable beneficial effect can also be that, when a composition of the invention is administered to a subject before symptoms to be treated are observable, the symptoms are prevented from occurring or subsequently occur to a lesser degree than without administration of the composition.

In some embodiments, a therapeutically effective amount of creatine or a derivative thereof of Formula (2) or a pharmaceutically acceptable salt thereof or a solvate thereof of the invention can alleviate or eliminate pain, itch, eczema or discomfort associated with an inflammatory cosmetic or medical condition, disorder, or disease in a human subject to be treated or who has been treated, by at least about 20%, for example, by at least about 30%, by at least about 40%, by at least about 50%, by at least about 60%, by at least about 70%, by at least about 80%, by at least about 90%, or about 100%, preferably by at least about 25%; by at least about 50%, by at least about 75%, or by at least about 90% to 100%, relative to the condition or discomfort, associated with pain prior to administration of a composition of the invention.

In some embodiments, the composition comprises at least 1% by weight or volume, based on a total weight or volume of the composition, of creatine or a derivative thereof of Formula (2) or a pharmaceutically acceptable salt thereof or a solvate thereof according to the invention. In certain embodiments, a topical composition of the invention comprises about 1% to about 10% by weight or volume, based on a total weight or volume of the composition, of creatine or a derivative thereof of Formula (2) or a pharmaceutically acceptable salt thereof or a solvate thereof according to the invention, such as, about 1%, 1.5% 2%, 2.5%, 3%, 3.5%, 4%, 4.5%, 5%, 5.5%, 6%, 6.5%, 7%, 7.5%, 8%, 8.5%, 9%, 9.5%, or 10%, or any number in between, by weight or volume.

Compositions of the invention can be formulated for administration according to any method known in the art. Typically, the compositions are formulated for topical administration or systemic administration. The topical application includes administration to skin, mucous membranes of the conjunctiva, nasopharynx, oropharynx, vagina, urethra, rectum, and anus. The systemic administration includes oral (enteral) administration and parenteral injections. The parenteral injections include intravenous injection or infusion, intra-arterial injection, subcutaneous injection, intramuscular injection, and intra-articular injection. Other routes of administration include sublingual administration, oral or nasal spray, under the tongue, from oral mucosa bypassing the portal circulation, and pulmonary adsorption by inhaling and absorbing through the respiratory tract.

In some embodiments, the composition is for topical administration.

In some embodiments, the composition is for systemic administration, preferably parenteral injection, more preferably subcutaneous injection.

In some embodiments, the composition is for oral or nasal spray, or sublingual administration.

Compositions according to embodiments of the invention can further comprise a pharmaceutically or cosmetically acceptable carrier. Pharmaceutically and cosmetically acceptable carriers are well known to those of ordinary skill in the art and one of ordinary skill in the art would be able to select an appropriate pharmaceutical or cosmetically acceptable carrier for inclusion in a composition of the invention depending on a variety of factors including the type of composition, e.g., solution (aqueous or anhydrous), cream, etc., and intended route of administration, e.g., topical, systemic, etc., based on general knowledge in the art in view of the present disclosure.

In some embodiments, a composition of the invention is formulated in any manner suitable for topical administration to a human subject, preferably for topical application to skin of a human subject. For example, for topical application, a composition comprising creatine or a derivative thereof of Formula (2) or a pharmaceutically acceptable salt thereof or a solvate thereof according to the invention can be formulated as a solution, gel, lotion, cream, oil-in-water emulsion, water-in-oil emulsion, ointment, shampoo, spray, stick, powder, mask, pads, mouth rinse or wash, or other form acceptable for use on skin, oral mucosa, mouth or gums.

In some embodiments, a composition of the invention is formulated in any manner suitable for systemic administration to a human subject, preferably for parenteral injection including subcutaneous injection to a human subject. For parenteral injections, creatine or a derivative thereof of Formula (2) or a pharmaceutically acceptable salt thereof or a solvate thereof is prepared in a solution or suspension under sterilized conditions in concentration from about 1% to about 10%, by weight or volume in water, ethanol, propylene glycol, a mixture thereof, or in other vehicle or carrier. The other vehicle or carrier includes peanut oil, soybean oil, mineral oil, sesame oil, and the like.

In some embodiments, the composition further comprises other pharmacological agents, such as a cosmetic, pharmaceutical or other topical agent. The cosmetic, pharmaceutical or other topical agent can be added to the inventive composition for synergetic or synergistic effect.

According to embodiments of the present application, examples of the topical agent include, but not limited to, local analgesics and anesthetics, anti-microbial agents, anti-inflammatory agents, anti-aging and anti-wrinkle agents, sunblock and sunscreen agents, vitamins, and corticosteroids.

In some embodiments the topical agents include, but not limited to: acetaminophen, 2-acetoxybenzoic acid; benzophenone; betamethasone dipropionate; bupivacaine; butoconazole; caffeic acid; caffeine; clobetasol propionate; clotrimazole; dapsone; erythromycin; gluconic acid, gluconolactone, glucuronic acid, glucuronolactone, glycolic acid; hydrocortisone; hydrocortisone 21-acetate, hydrocortisone 17-butyrate, hydrocortisone 17-valerate, hydrogen peroxide; hydroquinone; kojic acid; lactic acid; lidocaine; mandelic acid; minoxidil; retinal; 13-cis-retinoic acid; retinoic acid; retinol; retinyl acetate; retinyl palmitate; and triamcinolone acetonide.

In yet general aspect, the present application relates to a method for treating pain, itch, or eczema, or inflammation in a human subject in need thereof, the method comprising administering to the human subject a composition comprising creatine or a derivative thereof of Formula (2):

$H_2NC(=NR_1)N(CH_3)CH_2COR_2$     Formula (2)

or a pharmaceutically acceptable salt thereof or a solvate thereof, and optionally a pharmaceutically or cosmetically acceptable carrier, wherein, $R_1$ is H or an acyl radical having up to 29 carbon atoms; $R_2$ is H, $OR_3$, $NHR_4$, or any other amino group containing radical having up to 10 carbon atoms; $R_3$ is H, an alkyl, aralkyl or aryl radical, wherein the alkyl, aralkyl or aryl radical has up to 19 carbon atoms; and $R_4$ is H, OH, an alkyl, aralkyl, aryl or acyl radical, wherein the alkyl, arakyl, aryl or acyl radical has up to 19 carbon atoms. Any composition described in the present application can be used in the method.

In some embodiments, $R_1$ is H, Ac (acetyl), Ba (butanoyl), Bo (benzyloxycarbonyl), Bz (benzoyl), Fo (formyl), Hd (hexadecanoyl), He (hexanoyl), Hp (heptanoyl), Le (linoleic), Ln (linolenic), Na (nonanoyl), Oa (octanoyl), Pa (propanoyl), Pc (phenylacetyl), Pe (pentanoyl), or Pg (pyroglutamyl).

In some embodiments, $R_1$ is H, Ac (acetyl), Bz (benzoyl), or Pc (phenylacetyl).

In some embodiments, $R_2$ is H, $OR_3$, or $NHR_4$, preferably H, OH, OEt, $OC_3H_7$, NHOH, or $NH_2$.

In some embodiments, $R_2$ is $NHNHR_5$; and $R_5$ is H, OH, an alkyl, aralkyl, aryl or acyl radical, wherein the alkyl, arakyl, aryl, or acyl radical has up to 19 carbon atoms.

In some embodiments, $R_2$ is $NHNH_2$, NHNHAc, $NHCONH_2$, $NH(C=NH)NH_2$, $NH(C=NH)NHNH_2$, $NHNH(C=NH)NH_2$, $NH(C=NH)NHNHAc$, NHNH$(C=NH)NHAc$, or $(H_3C)_2N(C=N)N(CH_3)_2$.

In certain embodiments, $R_2$ is $NH(C=NH)NH_2$, $NH(C=NH)NHNH_2$, or $NHNH(C=NH)NH_2$.

Representative creatine or the derivatives in Formula (2) are listed in Table 1 described above.

In a particular embodiment, the composition comprises N-acetyl ethyl creatinate.

In another particular embodiment, the composition comprises creatine monohydrate.

In another particular embodiment, the composition comprises HC1 salt of ethyl creatinate.

In some embodiments, the composition is administered topically.

In some embodiments, the composition is administered systemically, preferably by parenteral injection, more preferably by subcutaneous injection.

In some embodiments, the composition is administered by oral or nasal spray, or sublingual administration.

According to embodiments of the present application, the method comprises administering to the human subject a therapeutically effective amount of creatine or a derivative thereof of Formula (2) or a pharmaceutically acceptable salt thereof or a solvate thereof according to the invention, or a composition comprising the same. Creatine or a derivative thereof of Formula (2) or a pharmaceutically acceptable salt thereof or a solvate thereof, or any composition described herein, is suitable for use in the methods of the invention.

According to embodiments of the of the present application, the composition can be administered alone or optionally in combination with another pharmacological agent. The composition and the other pharmacological agent can be administered simultaneously or sequentially to provide synergetic, synergistic, or enhanced effects. Examples of the other pharmacological agent suitable for use in the methods of the invention include, but are not limited to, acetaminophen, 2-acetoxybenzoic acid; benzophenone; betamethasone dipropionate;

bupivacaine; butoconazole; caffeic acid; caffeine; clobetasol propionate; clotrimazole; dapsone; erythromycin; gluconic acid, gluconolactone, glucuronic acid, glucuronolactone, glycolic acid; hydrocortisone; hydrocortisone 21-acetate, hydrocortisone 17-butyrate, hydrocortisone 17-valerate, hydrogen peroxide; hydroquinone; kojic acid; lactic acid; lidocaine; mandelic acid; minoxidil; retinal; 13-cis-retinoic acid; retinoic acid; retinol; retinyl acetate; retinyl palmitate; and triamcinolone acetonide.

The compounds and compositions according to the invention can provide analgesic effects, and can thus be used to treat pain, itch, eczema or other discomfort in a human subject. In addition, the compounds and compositions according to the invention reduce or eliminate erythema, edema and tissue distortions associated with inflammation.

In some embodiments, the method can alleviate or eliminate the pain, itch, eczema or other discomfort in a human subject in a human subject.

In some embodiments, the pain, itch, eczema or other discomfort is associated with an inflammatory cosmetic or medical condition, disorder, or disease.

In particular embodiments, the pain, itch, eczema or other discomfort is associated with a medical condition, disorder or disease including arthritis (e.g., osteoarthritis, psoriatic arthritis, rheumatoid arthritis, etc.), headache (e.g., migraine headache, hangover headache, acute common headache, etc.), dental pain, itch, eczema, lipoma, muscle pain, eczema, pharyngitis, sprain, trauma, sunburn, mosquito bites, and thermal burns.

The phrase "associated with," as used herein with reference to pain, itch, or eczema and any particular disease, disorder, condition, symptom or syndrome, means that the pain, itch, or eczema is caused by the disease, disorder, condition, syndrome or symptom, or experienced, observed, or perceived by the human subject at substantially the same time as the occurrence of the disease, disorder, condition, syndrome or symptom. For example, in one embodiment, "pain associated with arthritis" means that the pain, itch, or eczema in the human subject is caused by the arthritis. In another embodiment, "pain associated with arthritis" means that the pain, itch, or eczema is experienced, observed, or perceived by the human subject at substantially the same time as the occurrence of the arthritis in the human subject.

In particular embodiments, the method is for treating pain in the human subject.

In more particular embodiments, the pain is associated with a medical condition, disorder or disease including arthritis (e.g., osteoarthritis, psoriatic arthritis, rheumatoid arthritis, etc.), headache (e.g., migraine headache, hangover headache, acute common headache, etc.), dental pain, itch, eczema, lipoma, muscle pain, eczema, pharyngitis, sprain, trauma, sunburn, mosquito bites, and thermal burns.

Dosages and dosing frequency are determined by a trained medical professional depending on the analgesic effectiveness of creatine or a derivative thereof of Formula (2) or a pharmaceutically acceptable salt thereof or a solvate thereof, or a composition comprising the same that is used, the characteristics of the particular formulation, and the identity and severity of pain, itch, eczema or other discomfort treated. One of ordinary skill in the art will be able to determine appropriate treatment dosage and frequency based on general knowledge in the art in view of the present disclosure. The compound or the composition according to the invention can be administered as often as needed to eliminate or eliminate pain, itch, eczema, or other discomfort.

In view of the present disclosure, standard procedures can be performed to evaluate the analgesic effect of creatine or a derivative thereof of Formula (2) or a pharmaceutically acceptable salt thereof or a solvate thereof, or a composition comprising the same that is administrated to a human subject, thus allowing a skilled artisan to determine the therapeutically effective amount, the route of administration, the dosing frequency, etc. Because pain, itch; or eczema is a subjective condition or symptom based on perception, sensation or reaction, the human subject to be treated is preferably able to participate in the evaluation of the therapeutic efficacy of creatine or a derivative thereof of Formula (2) or a pharmaceutically acceptable salt thereof or a solvate thereof, or a composition comprising the same.

For example, clinical evaluation of analgesic effectiveness can be defined as 1+ (25%), which represents partial relief of pain, itch, or eczema for less than 6 hours; 2+ (50%), which represents substantial but incomplete relief of pain, itch, or eczema for less than 6 hours; 3+ (75%), which represents complete relief of pain, itch, or eczema for less than 6 hours and 4+ (90-100%), which represents complete relief or eradication of pain, itch, or eczema for more than 6 hours. Such clinical evaluation can be used to determine the analgesic effectiveness of administration (e.g., topical administration or systemic administration) of creatine or a derivative thereof of Formula (2) or a pharmaceutically acceptable salt thereof or a solvate thereof, or a composition comprising the same.

Based on the clinical findings described herein, topical or systemic administration of creatine or a derivative thereof of Formula (2) or a pharmaceutically acceptable salt thereof or a solvate thereof, or a composition comprising the same are therapeutically effective for treating pain, itch, or eczema of arthritis, inflammation, and other conditions, disorders or syndromes associated with inflammation in cancers, infections, and inflammatory disorders of the immune system, nervous system, musculoskeletal system, or other system.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the following Examples, test results and appended claims.

EXAMPLES

The following examples of the invention are to further illustrate the nature of the invention. It should be understood that the following examples do not limit the invention and that the scope of the invention is to be determined by the appended claims.

Example 1: Formulation Vehicles

As used in the present application, "WEP 442" represents water 40 parts, ethanol 40 parts and propylene glycol 20 parts by volume; "WEP 433" represents water 40 parts, ethanol 30 parts and propylene glycol 30 parts by volume; "WEP 244" represents water 20 parts, ethanol 40 parts and propylene glycol 40 parts by volume; "EP 55" represents an anhydrous composition with ethanol 50 parts and propylene glycol 50 parts by volume; and "WP 82" represents water 80 parts and propylene glycol 20 parts by volume.

Example 2: Evaluation of Analgesic Effectiveness

Five scales were used to evaluate the efficacy of analgesic effect: 0 (zero) for no effect; 1+ (25%), which represents partial relief of pain, itch, or eczema for less than 6 hours; 2+ (50%), which represents substantial but incomplete relief of pain, itch, or eczema for less than 6 hours; 3+ (75%), which represents complete relief of pain, itch, or eczema for less than 6 hours; and 4+ (90-100%), which represents complete relief or eradication of pain, itch, or eczema for more than 6 hours Example 3: Preparation of Formulation of C12X4WEP442

HCl salt of ethyl creatinate 1 gram was dissolved in 24 ml of a solution prepared from water 40 parts, ethanol 40 parts and propylene glycol 20 parts by volume. L-arginine 0.15 gram was then added to the resulting solution raise the pH from 2.7 to 5.2. The formulation thus obtained contained 4% ethyl creatinate and was referred to as C12X4WEP442.

Example 4: Effects on Osteoarthritis

A female subject, age 68, with worsening osteoarthritis of both knees, who had been advised to have surgical knee replacement, sought advice on possible alternative treatments. She was provided with the following formulations for topical applications:

Formulation A:

| Component | Percentage (%) |
| --- | --- |
| Creatine monohydrate | 2 |
| Malic acid | 0.1 |
| Sodium lauryl sulfate | 2 |
| Polysorbate 80 | 0.6 |
| Propylene glycol | 3 |
| Mineral oil | 0.3 |
| Water | 92 |
| Final pH 4.6 | |

Formulation B:

| Component | Percentage (%) |
| --- | --- |
| Creatine monohydrate | 2 |
| Vinegar | 4 |
| Sodium lauryl sulfate | 2 |
| Polysorbate 80 | 0.6 |
| Propylene glycol | 3 |
| Mineral oil | 0.4 |
| Water | 88 |
| Final pH 4.5 | |

Subject reported that the formulation A and formulation B were equally effective in providing pain relief, of estimated 80%, within 3-8 minutes after application to the knees and lasting for 4-5 hours. Pain relief has been sufficient for her to postpone consideration of knee replacement until the COVID-19 pandemic is subdued.

Example 5: Effects on Back Pain

A female subject, age 62, with aggravating lower back pain of 2-3 years duration, was provided 8 ounces of Formulation A (Example 4) to be applied to the lower back in late afternoon when her lower back pain intensified from mild to substantial. Pain subsided completely within 3-4 minutes, not returning until early afternoon the next day, beginning as mild and worsening during the afternoon hours.

Subject was then instructed to apply the Formulation A to the entire lower back area in late morning, before lower back pain had started or was of minor degree. When applications were made at this early time, no disturbing pain or discomfort developed later on. After a test period of a month subject reported that she had become almost entirely free of lower back pain day after day.

The foregoing events and observations show that creatine applied topically can prevent the development of lower back pain as well as alleviate it. The mechanism of these actions is unclear. But these effects suggest that topical creatine application can be put to practical clinical therapeutic use.

Example 6: Effects on Psoriatic Arthritis

A female subject, age 60, with worsening psoriatic arthritis over the past decade, was provided the same Formulation A of the foregoing Example 4. Applications of the formulation as often as needed to affected joints of left shoulder, both wrists and right ankle provided complete relief of pain within 3-5 minutes and lasted for 5-7 hours.

To provide similar complete relief of pain, in multiple finger joints nitrile gloves containing about 0.2 ml of the formulation in each glove finger were worn for 10-15 minutes, which provided complete pain relief for 3-5 hours. Subject needed to repeat the procedure 2-3 times daily to maintain relief of finger pain. In addition to the relief of finger pain, swelling (edema) of the arthritic joints became reduced to the degree that rings for her fingers that could not be worn earlier could again be worn.

Example 7: Effects on Osteoarthritis of Fingers, Wrists, Shoulder, Neck

A male subject, age 92, with career as carpenter/builder, who suffered consequent osteoarthritis of fingers, wrists, left shoulder and neck, was provided the same Formulation A of the foregoing Example 4. Applications of the formulation to the sites of pain for an interval of 3 weeks relieved pain completely or near completely for 48 hours, including the relief of pain throughout the night, with sleep undisturbed by body movements during sleeping hours. After 2 weeks of use pain was relieved for longer and longer periods, i.e. for days. After the last application the fingers and wrists were pain free for nearly a month.

Such effect could be due to a sustained anti-inflammatory action since inflammation is the actual cause of pain in numerous disorders.

Example 8: Effect on Post Fracture Acute Ankle Pain

A 50 year old female subject with a history of fractured left ankle seven years earlier, who had worn a plaster cast for several weeks at that time, related that for the past three months disturbing and increasing pain in the left ankle, which was occurring daily and was disturbing her sleep every night. Oral ibuprofen did relieve the pain for several hours, but the pain always recurred. She was provided 8 ounces of the above Formulation A (Example 4), to be applied to the painful ankle as needed. Two weeks later she reported that a single application of the formulation completely relieved pain, itch, and eczema within five minutes, and lasted for 7 hours or longer. Six months later she reported that pain relief from a single application had lasted longer and longer and that the ankle finally had become completely without pain for about three months.

The foregoing results indicate that formulations of creatine monohydrate applied topically have strong efficacy in clinical use for control of pain secondary to inflammation.

Example 9: Effect on Painful Swelling of Knee Joint

A 59 year old female subject with relentless painful swollen right knee for 3-4 years, not relieved by oral ibuprofen, was tested and rated analgesic efficacy of the three following formulations applied topically to the knee.

Formulation C12-3:

| Component | Percentage (%) |
| --- | --- |
| HCl salt of ethyl creatinate | 3 |
| Meglumine | 3 |
| Water:ethanol:propylene glycol = 4:3:3 | 94 |
| Final pH 7.5 | |

Rating: This formulation was rated lowest among the three tested formulations. Complete relief of pain, itch, and eczema occurred within 5 minutes. Duration of relief was 6-8 hours. Three to four applications daily were required for sustained pain relief.

Formulation C15-1:

| Component | Percentage (%) |
| --- | --- |
| N-acetyl ethyl creatinate | 1 |
| Water:propylene glycol = 8:2 | 99 |
| Final pH 5.2 | |

Rating: This formulation was rated next best and very good. Complete relief of pain occurred within 2-3 minutes and lasted for more than 12 hours.

Formulation C15-2:

| Component | Percentage (%) |
| --- | --- |
| N-acetyl ethyl creatinate | 2 |
| Water:propylene glycol = 8:2 | 98 |
| Final pH 5.3 | |

Rating: This formulation was judged to be the best and outstanding. Complete relief of pain occurred within 2-3 minutes and lasted at least for 24 hours.

The foregoing results indicate that chemical derivatives of creatine applied topically have very strong analgesic efficacy in clinical use for control of pain in different disorders.

Example 10: Effect on Acute Knee Pain

A 43 year old female subject with painful left knee gave a history of physical trauma to the left knee while cleaning her house. Degree of pain was sufficiently intense that it required her to wear a knee brace throughout the day, daily. One week later she helped remove heavy snow from outside access ways, during which time she sustained a traumatic twisting of the knee that resulted in intensified pain of the knee. The subject was provided a formulation of N-acetyl ethyl creatinate 1.5% dissolved in water: propylene glycol 8:2 for topical application. At follow-up 5 days later she reported that within about 2 minutes after application of the formulation to the knee, pain in the knee completely vanished "like a miracle". Pain had not recurred at the time of her report 10 days later. These results indicate that a derivative of creatine of the present invention applied topically in clinical use has very strong efficacy against inflammation and concomitant pain secondary to physical trauma of a joint.

Example 11: Effect on Acute Neck Pain

A 44 year old male subject who had shoveled heavy snow all day, throwing the snow mostly to left, upon arising from bed the next morning experienced acute pain in the left side of his neck that intensified as he attempted to move his head in any direction. His spouse had in her possession the formulation of N-acetyl ethyl creatine 1.5% dissolved in water: propylene glycol 8:2 that she had topically used the previous day to obliterate pain in her left knee as described in Example 10, which formulation she applied to the neck of her husband. Within 2 minutes his neck pain subsided completely and did not return.

This result affirms that a derivative of creatine of the present invention applied topically has very strong efficacy in clinical use for control of pain secondary to muscle inflammation due to stress of excessive muscle use.

Example 12: Effect on Multiple Pain, Itch, Eczema Sites

The subject in this Example was a 59 old female with pain emerging in multiple anatomic sites over the past decade. Current persistent disabling pain, itch, eczema problems include lower back pain and pain in the right hip. For both conditions she compared the pain relieving efficacy of the following two topically applied formulations.

Formulation 1:

| Component | Percentage (%) |
| --- | --- |
| Creatine monohydrate | 2.5 |
| Sodium lauryl sulfate | 1.5% |
| Mineral oil | 1% |
| Vehicle:water:glycerin:propylene glycol 5:2:3 | |

Formulation 2 was:

| Component | Percentage (%) |
| --- | --- |
| N-acetyl ethyl creatine | 1.5 |
| Vehicle:water:propylene glycol 8:2 | |

After topically testing for the efficacy of each formulation to relieve lower back pain and hip pain, she reported that Formulation 1 relieved in both sites by an estimated degree of 75% that lasted for 2-3 hours, and that Formulation 2 relieved pain completely and lasted for 4-5 hours.

These results indicate that creatine and derivative thereof applied topically can substantially relieve pain of inflammation of different kinds. Such eradication of the symptom of pain that often occurs with inflammation, by creatine and related compounds introduces a new category of non-steroidal anti-inflammatory agents, as well as a new category of anti-pain agents, both of which can be viewed as having possible immense clinical use.

Example 13: Effect on Rheumatoid Arthritis Fingers

A 60 year old female subject noted changes in her fingers that appeared to be compatible with the diagnosis of early rheumatoid arthritis in autumn of the year. At about one month later there appeared over the terminal interphalangeal joint of the left third finger a raised inflammatory nodule compatible with the diagnosis of a rheumatoid nodule. The nodule was injected with 0.15 ml of a 2% aqueous solution/ suspension of creatine monohydrate once weekly for four injections. Over a period of 9 weeks the nodule resolved almost completely, leaving a faint erythema at the site. Thereafter, for a period of one month, the subject wore a nitrile glove containing a few drops N-acetyl ethyl creatine 3% dissolved in water: propylene glycol 8:2 for about an hour twice daily on the left hand only. After another two months the following benefits had occurred:
- The left hand was said to feel much better than the right hand;
- The site of the nodule remained a slightly erythematous flat macule;
- The left hand and fingers were completely flexible; the flexibility of the right hand was restricted; and
- In making a tight fist of both hands, the size of the left fist was visibly smaller than that of the right. In making the fists the subject reported that the left fist was pain free whereas the right fist was substantially painful.

The foregoing results indicate that creatine injected into a rheumatoid nodule can resolve the nodule and that a derivative of creatine applied topically is associated with improvements of the signs and symptoms of rheumatoid arthritis. These events suggest that creatine and derivatives thereof can be viewed as having possible immense therapeutic benefit in clinical management of rheumatoid arthritis.

Example 14: Effects of Subcutaneous Injection of Creatine Over Sites of Spinal Pain A physician subject, age 98, with continually worsening osteoarthritis of multiple joints for 15-16 years, prepared a sterile aqueous injectable solution/suspension of 2% creatine monohydrate. Under his direction, medical assistants were instructed on techniques to give subcutaneous injections of the 2% aqueous solution/suspension with either a 1 ml syringe with 27 gauge 13 mm needle or with a 1 ml insulin syringe with 30 gauge 8 mm needle.

Five intervertebral painful sites of arthritis of cervical and thoracic spine, identified by finger pressure, received a single injection of 0.3 ml of the solution. All sites/areas became pain free within 2-3 hours after injection, and without receiving any further therapy, remained pain free for 7 weeks.

The foregoing results indicate that creatine monohydrate and its subcutaneous injections over sites of arthritic or arthritic-like pain, both of the present invention, are strongly beneficial in clinical use as treatment of spinal arthritis or analogous inflammatory conditions of the spine.

Example 15: Effects of Subcutaneous Injection of Creatine Over Ankle with Psoriatic Arthritis A diabetic female subject, age 61, with psoriasis for over 4 decades, and worsening psoriatic arthritis for about 10 years, presented with an acutely painful, swollen and erythematous right ankle. Using a 1 ml insulin syringe with short needle she injected 0.5 ml of the 2% creatine monohydrate as described above into a subcutaneous site of the anterior ankle. Ankle pain completely resolved within about 30 minutes. The edema and erythema of the ankle completely resolved within a week. Four weeks after the injection the ankle remained pain free, was of normal appearance, and was completely functional as a normal ankle.

The foregoing results indicate that creatine and its subcutaneous injection over sites of inflammation and pain, both of the present invention, are strongly anti-inflammatory and relieve pain associated with such inflammation.

Example 16: Effects of Subcutaneous Injection of Creatine for Relief of Hip Pain A female subject, age 59, who for several weeks was experiencing disabling arthritic pain in the right hip joint, was given two subcutaneous injections of a sterile 2% aqueous solution/suspension of creatine monohydrate over the point of pain, 0.5 ml given first, and 0.6 ml given five days later. Complete relief of pain lasted for 2 weeks before a returning mild pain was sensed, which slowly worsened over the next week. A third subcutaneous injection of 0.7 ml of the 2% creatine monohydrate solution/suspension was given over the point of joint pain elicited by finger pressure. Complete relieve of pain occurred within 3-4 hours. Hip remained pain free for another 2 weeks.

The foregoing results indicate that creatine monohydrate and its subcutaneous injection over a site of pain associated with inflammation are strongly analgesic in clinical use in relieving hip pain.

Example 17: Effects of Creatine for Post Dental Surgery Pain

A male subject, age 88, had three teeth, #23, 24 and 25 extracted at 12 noon, then had two implants posted immediately after. At about 6 pm, subject started to feel pain in the gum area after lidocaine anesthesia wore off. Subject was instructed to use Stellalife® antimicrobial mouth rinse several times, which however provided no pain relief. The subject took about 1 gram creatine monohydrate powder into mouth. The powder, as it dissolved in saliva, was rinsed for approximately 5 minutes, then swallowed. The dental pain stopped in about 20 minutes, and relief lasted for 8 hours.

The above result shows that creatine can be effective in eradicating dental pain on topical application to the gum area.

Example 18: Effect of Whole Body Application

A 98 year old male subject with continually worsening very painful osteoarthritis of multiple joints for 15-16 years prepared the following formulation:

N-Acetyl Ethyl Creatinate (C15): Water:Propylene glycol:Mineral Oil:Sodium lauryl sulfate 68:30:0.5:1.5:38.

After taking a morning shower, the entire 40 ml formulation was applied by himself and his assistants to his entire body, except the scalp. Within about 5 minutes all pain ceased in all previously painful joints, i.e., spine, right shoulder, right elbow, knees and feet. The subject was without any sense of pain for 4.5 hours when mild painful discomfort in the neck was sensed. Over the next 3 hours pain in all joints returned to usual substantial levels.

The foregoing results suggest that a sufficient amount of N-acethyl ethyl creatinate may have been absorbed percutaneously to provide a systemic effect.

Example 19: Effects of Abdominal Subcutaneous Injections

A 98 year old male physician subject with continually worsening, for 15-16 years, painful osteoarthritis of numerous joints (almost entire spine, wrists, right shoulder, knees and most recently the feet) on one day at 11:30 AM self injected subcutaneously the right abdominal area with 3 ml of a sterile aqueous solution that he had prepared containing N-acetyl ethyl creatinate 1%, arginine 0.25%, pH 7. Using 1 ml insulin syringes with short 8 mm needles 1 ml of the solution was injected into each of 3 sites. Ten minutes later his whole body was 95+% pain free and remained so for 3.5 hours when pain was sensed to be returning. Pain in usual severity returned within another 20-30 minutes.

The next day at 9:00 AM the subject injected 5 sites, each with 1 ml of the same solution. Within 10 minutes his whole body again was 95+% pain free. This almost complete pain free state was maintained for 4 hours when very mild pain in the knees was sensed. Pain in knees and in cervical spine returned to usual degree of severity within an ensuing period of about 20 minutes. The foregoing results show that whole body pain relief of inflammatory joint pain of arthritis can be achieved by a creatine derivative administered subcutaneously.

Example 20: Rapid Pain Relief and Resolution of Aphthous Ulcers (Canker Sores) by Topical Application of N-Acetyl Ethyl Creatinate (C15)

Two eroded painful sites 2-3 mm in diameter on the right side of the tongue worsened over 2 days in a 98 year old male subject. At bedtime of the 2nd day, the subject topically applied C15 3% in water: propylene glycol 8:2. Complete pain relief occurred within less than a minute. The sites remained pain free throughout the night and did not return. No clinical sign of the lesions could be detected next day by subject, nor by two associates.

The foregoing experience suggests that topical C15 can be efficacious in general routine therapy of canker sores.

Example 21: Subcutaneous Injection of N-Acetyl Ethyl Creatinate (C15) over Bunion Leads to Gradual Resolution of the Deformity A 50 year old female subject presented with bunion on right foot that has been enlarging over the past decade. Weekly subcutaneous injections over the bunion of C15 1.5% in aqueous solution has revealed the bunion has undergone a distinct resolution in mass. Weekly injections will be continued for another month or two to determine whether complete resolution will be achieved.

Example 22: Instant Complete Relief of Pain of Thermal Burns by Topical N-Acetyl Ethyl Creatinate (C15)

One subject, a 62 year old male, spilled boiling hot water on his left hand. Within a couple hours pain was intense. He then applied 4% solution of N-acetyl ethyl creatinate (C15) dissolved in water:ethanol:propylene glycol 5:3:2 which he had been using to relieve pain over a lateral meniscus. He reported there was immediate relief of the burn pain for periods of 4-5 hours. Such application was continued over the next several days until the burn pain disappeared spontaneously.

A second subject, a 60 year old female, burned her forearm where she accidentally touched the hot oven rack. She immediately applied 9% solution of N-acetyl ethyl creatinate (C15) dissolved in water:ethanol:propylene glycol 5:3:2 that she was using for topical treatment of her rheumatoid arthritis. Burn pain was completely instantly relieved, lasting for 4-5 hours. Repeated application were applied over the next 3 days, until the burn pain spontaneously ceased. These results indicate that topical applications of C15 could be used to routinely relieve burn pain.

Example 23: Pain of Dystonia Relieved by Local Subcutaneous Injections of N-Acetyl Ethyl Creatinate (C15), Relief Lasting for 2-3 Weeks A 59 year old female subject presented with muscular pain of her upper right back which had been diagnosed by neurologist as a symptom of dystonia (which also caused involuntary tic movements of her head). Five sites of the upper back were injected with 0.3 ml C15 in aqueous solution using insulin syringes with 30G short needles. Complete relief of pain occurred within the next hour, and such relief lasting for 2 weeks. At that time the injections were repeated just before she departed on a trip to Europe. By phone she reported that relief of pain was lasting beyond two week period.

Example 24: Effects of N-Acetyl Ethyl Creatinate (C15) on Osteoarthritis of Various Body Joints Elbow:

A 65 year old male subject presented with a history of painful right elbow for several weeks. He was provided with a topical solution of C15 8% in WP 82. He has reported that application of this solution to the elbow relieved pain instantaneously completely lasting for 5-6 hours.

A 99 year old male subject with a history of right elbow for several months applied the above same solution to the elbo w multiple times. No pain relieve was experienced.

On three other occasions, C15 1.5% aqueous solution 1 ml was injected subcutaneously in two lateral sites of the elbow and one site over extensor part of the elbow. Such injections provided complete relief of pain within an hour, lasting for 24-30 hours.

Shoulder:

The same 99 year old male subject above has had painful right shoulder for several months. Subcutaneous injections of 1 ml of the above solution on three occasions have provided complete relief of pain lasting for 6-7 days.

Spine:

The same 99 year old subject above topically applied an adhesive dressing, 5 cm wide and 30 cm long, saturated with a solution of C15 4% in WP 82 to the upper spine. This provided complete relief of pain within an hour, lasting for about 8 hours when the dressing was removed and found to be dry.

Over a period of 3 months, subcutaneous injections of 0.6 ml of the above C15 solution were injected subcutaneously into each of 5 intervertebral sites of the cervical and thoracic spine. On each of five occasions complete relief of pain lasting for 1-4 weeks, was experienced.

Knees:

The 65 year old male subject described above has reported that a solution of C15, 8% in WP 82 applied to a gauze wrapping of the knees and occluded with a plastic wrap has provided complete relief of pain for 8 hours of sleep. After removal in the morning he found that 85-90% diminishment of pain lasted for 7-8 hours. Several days later, a repeated application of the same procedure gave the same results.

The same 99 year old subject above, with severe osteoarthritis of the knees for 8-10 years, has found that topical application of C15, 8% in WP 82, even with occlusion provides only 3-4 hours of pain relief.

Example 25: Complete Pain Relief of Psoriatic Arthritis by Topical N-Acetyl Ethyl Creatinate (C15)

A 61 year old female subject with a 42 year history of psoriasis, and psoriatic arthritis for the past 8 years, was provided a topical solution of C15 4% in WP 82. Application of the solution to painful joints of the wrists, hands, fingers and ankles provided almost instantaneous, complete relief of pain that lasted for 6-24 hours. The subject has used topical formulations of C15 for over 12 weeks, comparing efficacy of 2%, 3.5% and 5% concentrations of C15. She has found that the most effective of the three has been 5% administered as a spray mist which has repeatedly provided complete pain relief for 24 hours.

These results suggests that topical application of C15 could be used as a routine clinical treatment of psoriatic arthritis pain.

Example 26: Relief and Resolution of Pain and Joint Deformities of Rheumatoid Arthritis (RA) by Topical and Intralesional Injection of C15

A 60 year old female subject, described in an earlier Example, after approximately 4 months of worsening symptoms, and finger joint enlargements on both hands, realized that she was rapidly developing RA, especially when a rheumatoid nodule enlarged over the terminal joint of the left forth finger to a size of approximately 1 cm in diameter, and about 3 mm thick. The nodule was initially injected with 0.15 ml of a 2% aqueous solution/suspension of creatine monohydrate once weekly for 4 injections. Over a period of 9 weeks the nodule resolved almost completely. Thereafter the subject wore a nitrile glove containing a few drops of C15 3-9% dissolved in WP 82 for an hour twice daily on the left hand only. After another 2 months C15 9% in WP 82 was topically applied by means of her wearing nitrile gloves containing the C15 solution for 1 hour twice daily. After 9 months of foregoing treatments both hands appear to be completely normal. It is intended for the subject to continue topical treatment in one form or another for an indefinite time forward.

Example 27: Ankle Sprain Pain Completely Relieved with Topical N-Acetyl Ethyl Creatinate (C15)

A 58 year old, female subject sprained her left ankle while hiking. Upon returning home she was provided with a solution of C15 4% dissolved in WP 82 which she applied to the ankle 2-3 times daily for 4-5 days, at the end of which time no ankle pain was detected and treatment was discontinued.

Example 28: Mosquito Bite Itch Completely Eradicated by Topical N-Acetyl Ethyl Creatinate (C15)

Six subjects, 2 males and 4 females, age 31-74 years, who had gathered for a back yard cookout, suffered multiple mosquito bites. One subject carried with her 2 ounces of C15 6% in WEP 532 which she shared with the five others for topical application to the pruritic urticarial mosquito bite lesions. All six subjects claimed that the itch was completely eradicated within about 1 minute. No itch returned.

Another subject, a 36 year old female, who had a history of being very sensitive to mosquito bites, was provided a solution of C15 6% in WEP 532 to be topically applied to sites of mosquito bite reactions. This solution was later applied to an intensely pruritic urticarial lesion, 1 cm in diameter, due to a mosquito bite. Within 1 minute of application all itch sensation was gone and did not return. Clinical evidence of the lesion began to fade about 3 minutes later, and at 5 minutes the subject had no sensory awareness of the lesion as it disappeared over the next 10-15 minutes.

The foregoing results indicate that C15 applied topically is therapeutically efficacious in eradicating itch associated with inflammation as occurring in the reaction to mosquito bites.

Example 29: Relief of Migraine Headache by Topical N-Acetyl Ethyl Creatinate (C15)

A 60 year old female subject, with a history of migraine headaches and associated symptoms, presented with a recurrent episode of such that had begun during her night of sleep. Symptoms included an intense frontal headache, and feeling of light dizziness, and nausea when she turned her head. She was provided a 9% solution of C15 dissolved in WEP 532 to be applied to the forehead and temporal areas as needed to relieve symptoms. Applications relieved symptoms within a few minutes. Relief lasted for 1-4 hours during the first day of use, and during the second day of use, the subject experienced a much longer period of relief of symptoms. On the morning of the third day, symptoms were very mild; and at the end of the day, following 3 more applications, symptoms were no longer detectable. She remained symptoms free over the next week of follow-up. The foregoing results show that symptoms of migraine can be relieved with repeated topical applications of N-acetyl ethyl creatinate, and can be completely eradicated after 2 days of use.

Example 30: Relief of Itch, and Improvement of Eczema by Topical N-Acetyl Ethyl Creatinate (C15)

A 31 year old male subject, with a 25 year history of eczema, was provided a topical formulation of 6% C15 in a lotion made up of hydrophilic ointment USP 35% diluted with 65% water. After ten days of topical application that relieved the itch for intervals of 1.5 hour up to 24 hours, the subject felt his eczema was undergoing resolution. He emphasized, however, that his eczema worsens in the autumn and winter, so his final judgment needs to be delayed from the summer season to several months later.

A 19 year old female subject with a 14 year history of eczema was provided the same lotion. After 2 weeks of applying the lotion topically, she has reported that itch was relieved completely for 24-48 hours following a single application.

A 40 year old female subject, with a history of eczema for 35 years, was provided the same solution. After 4 days of application to relieve itch as needed, she reported that itch was now negligible and that her skin was nearly entirely free of signs of eczema. She has expressed great gratitude and hopes that the same beneficial results will persist during the autumn and winter seasons.

The foregoing results indicate that topical N-acetyl ethyl creatinate can provide substantial improvement of physical signs of eczema, and can completely relieve itch associated with the disorder.

Example 31: Instantaneous Complete Relief of Sore Throat by Spray Mist of Aqueous N-Acetyl Creatinate (C15)

A 59 year old female subject, upon arising from bed in the morning, was acutely aware of a severe sore throat. Clinical examination about 4 hours later revealed her to have a deeply erythematous pharyngitis having no signs of bacterial infection. She was provided, in a 2 oz spray container, a 3% aqueous solution of C15 that she sprayed into her moth toward the inflamed pharynx. She reported an immediate complete relief of pain, which lasted for 25 minutes. Repeated spraying during the day were followed by longer pain free intervals. She reported that at 7 PM the last pain free interval had been 1 hour. Next morning the pharyngitis had improved, and the subject used spray mist less frequently.

The foregoing results indicate that C15 solution spray can be used clinically to relieve painful pharyngitis.

Example 32: Complete Relief of Itch of Dermatitis of Uncertain Etiology by Topical N-acetyl ethyl Creatinate (C15)

A 36 year old female subject who had worked planting a new rock and flower garden during the day, in the evening became acutely aware of an itch sensation in the lower back, just below the beltline. A photo of this area revealed it to be diffusely erythematous with scattered numerous punctate sites more intensely erythematous. Itch was completely relived by topical application of C15 4% in water: propylene glycol 8:2 that had been provided to her earlier. Itch relief lasted for 2-3 hours; three additional applications were made during the night. The dermatitis and itch resolved early next day. Etiology was not ascertained.

The above experience indicates that topical application of C15 relieves inflammatory itch.

Example 33: Relief of Post Trauma pain by Topical N-acetyl ethyl creatinate (C15)

A 65 year old subject was provided a 9% solution of C15 in WEP 532 for possible use against itch or pain. Several weeks later she sent by e-mail the following message:

"Yesterday I slammed the top of my hand accidentally against a door. That really hurt and I could barely move my hand. Started to ice it and then realized that I had decided to keep one bottle of the pain medicine here at the shore. Put the med on it and in a minute or two the pain went away. Like a miracle. Iced it after as I could tell a welt was forming. Again at bedtime I put a little of the pain med on it in case the earlier application wore off and iced again as it was a bit swollen. Looked red and maybe a little swollen this morning but no pain!"

The foregoing case account affirms the clinical value of C15, in a formulation to have on hand for emergency use.

Example 34: Complete Relief of Ankle Pain Five Months after Surgical Insertion of 10 Metal Screws into Fractured Bones by Topical N-2-acetoxybenzoyl Ethyl Creatinate (C26)

A 45 year old male subject with above described post trauma pain at the end of each day experienced painful discomfort in the pinned ankle. Prior applications of C15 formulations provided substantially relieve the pain but not completely. Application of a liquid formulation, vehicle of which was WEP 244, 6% C26 completely relieved the pain within 1 minute. Complete relief lasted nearly 24 hours.

At the end of the next day, the ankle was as painful as the days before. Subject applied 6% C20 in same liquid vehicle. Some relief did occur but not complete as with C26.

The foregoing results indicate that compounds of the present invention can be applied clinically to relive pain of different kinds.

Example 35: Complete Relief of Pain of Psoriatic Arthritis by Topical Application of N-benzoyl ethyl creatinate (C20) and by N-2-acetoxybenzoyl ethyl creatinate (C26)

A 60 year female subject with a 40 year history of psoriasis and several years of psoriatic arthritis topically applied the formulations cited in Example 34 above. Formulation of C20 was applied to both hands. The substantial pain of fingers, hands and wrists was completely relieved within about 2 minutes and lasted for 4 hours. The formulation of C26 was applied to the left ankle and foot, pain of which was relieved in about 5 minutes and lasted for 4-5 hours.

The foregoing results indicate that C20 and C26 solutions can be topically used clinically.

Example 36: Poison Ivy Dermatitis Itch Instantly and Completely Relieved by Topical Application of N-Acetyl Ethyl Creatinate (C15) and Dermatitis Resolved within Four Days A 55 year old male subject developed poison ivy dermatitis of his forearms about 18 hours after pruning bushes. Itch was intense at 24 hours when he applied C15 10% in a lotion made up of hydrophilic ointment USP 35% diluted with 65% water. Relief of itch was immediate, lasting for about 6 hours when C15 was again applied. Duration of itch relief next was for about 10 hours and the next for 12-15 hours. Relief was longer and longer from subsequent applications. Signs and symptoms of dermatitis were gone at 4 days.

The foregoing results indicate that C15 can be clinically used topically for treatment of poison ivy dermatitis.

Example 37: Relief of Itch, and Improvement of Eczema by Topical N-Acetyl Ethyl Creatinate (C15)

A 31 year old male subject, with a 25 year history of eczema, was provided a topical formulation of 6% C15 in a lotion made up of hydrophilic ointment USP 35% diluted with 65% water. After ten days of topical applications, itch was relieved for intervals of 1.5 hour up to 24 hours. The patient felt that his eczema was undergoing resolution during the summer. At the end of the following February, he reported that his eczema was still under almost complete resolution. Sites of itch were treated with prompt application of the above lotion which completely aborted further development.

A 19 year old female subject with a 14 year history of eczema was provided the same lotion. After 2 weeks of applying the lotion topically, she has reported that itch was relieved completely for 24-48 hours following single applications. Patient has moved from the area and has been lost to long term follow up.

A 40 year old female subject, with a history of eczema for 35 years, was provided the same formulation. After 4 days of application to relieve itch as needed, she reported that itch became negligible. With applications as needed her skin became nearly entirely free of signs of eczema. She expressed great gratitude and hoped that the same beneficial results would persist during the autumn and winter months. At the end of February she has reported that her skin has remained clear.

She reported: "I use it sparingly. If I feel any itch or see a little patch I put it on and it's gone like the next day. When it was hot and cold last week I would put a little on at night just in case and I never had an issue. It's so great. It's miraculous!"

The foregoing results indicate that C15 can be clinically used topically for treatment of eczema.

Example 38: Burning Itch Induced by Mucuna Pruriens Completely Relieved by Topical N-acetyl Ethyl Creatinate (C15)

Pods with beans were obtained from Afro Caribe Botanica, 16 separate specimens. Small round brushes marketed for interdental cleaning were used to collect spicules from the pods. Application to both volar and extensor surfaces of the forearm were made by intense rubbing of the skin with such brush containing spicules. Burning itch developed within 5-7 minutes. Topical application of C15 10% in a lotion made up of hydrophilic ointment USP 35% diluted with 65% water gave complete relief of itch within 1-2 minutes and was permanent. Participants in this study included the following;
1. A 99 year old male.
2. A 65 year old male.
3. A 45 year old male.
4. A 61 year old female.
5. A 44 year old female.

The foregoing results indicate that C15 can be clinically used topically for treatment of most intensive burning itch.

We claim:

1. A method for treating itch or eczema in a human subject in need thereof, the method comprising administering to the human subject a composition comprising a creatine derivative of Formula (2):

$$H_2NC(=NR_1)N(CH_3)CH_2COR_2 \quad \text{Formula (2)}$$

wherein, $R_1$ is an acyl radical selected from the group consisting of benzyloxycarbonyl, benzoyl, phenylacetyl, 2-acetoxybenzoyl, and pyroglutamyl; $R_2$ is $OR_3$; and $R_3$ is H, methyl, ethyl, propyl, or isopropyl.

2. The method of claim 1, wherein the creatine derivative is selected from the group consisting of:

$H_2NC(=NBz)N(CH_3)CH_2COOCH_3$, N-Benzoyl methyl creatinate $H_2NC(=NBz)N(CH_3)CH_2COOC_2H_5$, N-Benzoyl ethyl creatinate $H_2NC(=NAb)N(CH_3)CH_2COOCH_3$, N-(2-acetoxybenzoyl) methyl creatinate $H_2NC(=NAb)N(CH_3)CH_2COOC_2H_5$, N-(2-acetoxybenzoyl) ethyl creatinate $H_2NC(=NPc)N(CH_3)CH_2COOCH_3$, N-Phenylacetyl methyl creatinate $H_2NC(=NPc)N(CH_3)CH_2COOC_2H_5$, N-Phenylacetyl ethyl creatinate $H_2NC(=NPg)N(CH_3)CH_2COOCH_3$, N-Pyroglutamyl methyl creatinate $H_2NC(=NPg)N(CH_3)CH_2COOC_2H_5$, N-Pyroglutamyl ethyl creatinate $H_2NC(=NBo)N(CH_3)CH_2COOCH_3$, N-Benzyloxycarbonyl methyl creatinate $H_2NC(=NBo)N(CH_3)CH_2COOC_2H_5$, N-Benzyloxycarbonyl ethyl creatinate.

3. The method of claim 1, wherein the composition comprises N-benzoyl ethyl creatinate.

4. The method of claim 1, wherein the composition comprises at least 1% by weight or volume, based on a total weight or volume of the composition, of the creatine derivative of Formula (2).

5. The method of claim 1, wherein the composition comprises about 1% to about 10% by weight or volume, based on a total weight or volume of the composition, of the creatine derivative thereof of Formula (2).

6. The method of claim 1, wherein the composition is topically administered.

7. The method of claim 1, wherein the composition is systemically administered.

8. The method of claim 6, wherein the composition is administered by subcutaneous injection.

9. The method of claim 1, wherein the method provides anti-itch effect.

10. The method of claim 1, wherein the method further comprises administering another pharmacological agent to provide synergetic or synergistic effect, and the pharmacological agent is selected from the group consisting of acetaminophen, 2-acetoxybenzoic acid; benzophenone; betamethasone dipropionate; butoconazole; caffeic acid; caffeine; clobetasol propionate; clotrimazole; dapsone; erythromycin; gluconic acid; gluconolactone; glucuronic acid; glucuronolactone; glycolic acid; hydrocortisone; hydrocortisone 21-acetate; hydrocortisone 17-butyrate; hydrocortisone 17-valerate; hydrogen peroxide; hydroquinone; kojic acid; lactic acid; mandelic acid; minoxidil; retinal; 13-cis-retinoic acid; retinoic acid; retinol; retinyl acetate; retinyl palmitate; and triamcinolone acetonide.

11. The method of claim 1, wherein the eczema is selected from the group consisting of atopic eczema and inflammatory eczema.

* * * * *